United States Patent
Yager et al.

(10) Patent No.: US 6,176,990 B1
(45) Date of Patent: Jan. 23, 2001

(54) MICRO-ELECTROPHORESIS CHIP FOR MOVING AND SEPARATING NUCLEIC ACIDS AND OTHER CHARGED MOLECULES

(75) Inventors: Thomas D. Yager, Mississauga; Paul Waterhouse, Copetown; Alexandre M. Izmailov, Toronto; Bruno C. Maruzzo, Toronto; John K. Stevens, Toronto, all of (CA); Marina T. Larson, Yorktown Heights, NY (US)

(73) Assignee: Visible Genetics Inc., Toronto (CA)

(*) Notice: Under 35 U.S.C. 154(b), the term of this patent shall be extended for 0 days.

(21) Appl. No.: 08/973,933

(22) PCT Filed: Jun. 7, 1996

(86) PCT No.: PCT/US96/10110
§ 371 Date: Dec. 16, 1997
§ 102(e) Date: Dec. 16, 1997

(87) PCT Pub. No.: WO96/42013
PCT Pub. Date: Dec. 27, 1996

Related U.S. Application Data (60) Provisional application No. 60/000,036, filed on Jun. 8, 1995.

(51) Int. Cl.[7] .................................................. G01N 27/453
(52) U.S. Cl. .............................. 204/601; 204/605; 204/643
(58) Field of Search ................................. 204/451, 455, 204/456, 466, 547, 601, 605, 606, 616, 643; 435/6, 287.2

(56) References Cited

U.S. PATENT DOCUMENTS

| | | | |
|---|---|---|---|
| 4,390,403 | * | 6/1983 | Batchelder . |
| 4,908,112 | * | 3/1990 | Pace . |
| 5,011,586 | * | 4/1991 | Finney et al. . |
| 5,126,022 | * | 6/1992 | Soane et al. ............. 204/547 |
| 5,135,627 | | 8/1992 | Soane . |
| 5,627,022 | * | 5/1997 | Renfrew et al. . |

FOREIGN PATENT DOCUMENTS

| | | |
|---|---|---|
| 0 335 703 | 10/1989 | (EP) . |
| 0 359 589 | * 3/1990 | (EP) . |

(List continued on next page.)

OTHER PUBLICATIONS

Tanaka, n., et al, "Starburst Dendrimers as Carriers in Electrokinetic Chromatography", Chemistry Letters, pp. 959–962, 1992.

Zimmerman, S.C., et al, "Self–Assembling Dendrimers", Science, 271:1095–1098, Feb. 23, 1996.

(List continued on next page.)

* cited by examiner

*Primary Examiner*—William H. Beisner
(74) *Attorney, Agent, or Firm*—Oppedahl & Larson LLP (57) ABSTRACT

A microelectrophoresis chip comprises a substrate in which there are formed one or more channels, one channel for each sample to be evaluated. The channels extend for the length of the chip, a distance of generally around 1 cm, and are about 1 to 10 μm wide and 1 to 10 μm in depth. The channels are filled with a homogeneous separation matrix which acts as an obstacle to the electrophoretic migration of the charged molecules. Microelectrodes disposed in the channels are used to induce an electric field within the homogeneous separation medium. When a voltage is applied across two or more of the microelectrodes, the charged molecules are induced to move and separate according to the electric field density, the type of solvent film, and the charge, shape and size of the charged molecule. The chip may further comprise detectors, such as light polarization detectors, fluorescence emission detectors, biosensors, electrochemical sensors or other microcomponents which may include sites for enzymatic or chemical manipulation of the moved or separated charged molecules.

7 Claims, 7 Drawing Sheets

FOREIGN PATENT DOCUMENTS

| | | | |
|---|---|---|---|
| 0 365 321 | * | 4/1990 | (EP). |
| 0 391 674 | | 10/1990 | (EP). |
| 0 500 211 | | 8/1992 | (EP). |
| 0 653 631 | | 5/1995 | (EP). |
| 2 264 783 | * | 9/1993 | (GB) ................................ 204/643 |
| 61-026848 | * | 2/1986 | (JP) ................................ 204/616 |
| 3-167468 | * | 7/1991 | (JP) ................................ 204/616 |
| 90/02601 | * | 3/1990 | (WO) ................................ 204/616 |
| WO 91/12904 | | 9/1991 | (WO). |
| WO 93/00986 | | 1/1993 | (WO). |
| WO 96/35810 | | 11/1996 | (WO). |

OTHER PUBLICATIONS

Volkmuth, W.D. and R.H. Austin, "DNA electrophoresis in microlithographic arrays", Nature 358:600, 602, Aug. 1992.

Volkmuth, W.D., et al, "Trapping of branched DNA in microfabricated structures", Proc. Natl. Acad. Sci. USA 92:6887–6891, Jul. 1995.

MICRO-ELECTROPHORESIS CHIP FOR MOVING AND SEPARATING NUCLEIC ACIDS AND OTHER CHARGED MOLECULES

This application claims priority from U.S. Provisional Application Ser. No. 60/000,036 filed Jun. 8, 1995.

BACKGROUND TO THE INVENTION

The instant invention relates to methods and apparatus for electrophoretic movement and separation of samples of charged molecular species in a microelectrophoresis chip.

The principle of separating a mixed pool of charged molecules into separate species by electrophoresis through a separation matrix is well known in the art. Commercial apparatus are available for separation of proteins, nucleic acids and other biomolecules. In the most general format, a sample of biomolecules is loaded into a separation matrix (e.g., agarose gels and polyacrylamide gels, either with or without denaturing buffer solutions) at a loading site. Electrodes, e.g., solution electrodes, are placed at either end of the separation matrix. An electric field is the applied across the separation matrix, which causes electrically charged molecules in the sample migrate away from the loading site. The direction and extent of sample migration is a function of charge, size and shape of the molecule. (Current Protocols in Molecular Biology (ed. Janssen, K) John Wiley & Sons, Inc., 1987–94).

Electrophoresis can also be performed in tubes as described in International Patent Application No. WO91/12904 and European Patent Application No. 0 653 631 A2. Materials can be moved through these tubes in what amounts to a one-dimensional separation using variable electric fields generated by a plurality of electrodes disposed along the length of the tube.

Molecular species separated by electrophoresis may be simply observed and discarded (recorded patterns of separation provide important information such as in DNA sequencing: see Sanger et al. Proc. Natl. Acad. Sci. USA 74: 5463–5467 (1977)) or, in some applications, species are recovered from the separation matrix for further investigation. Recovery can be achieved in several well known ways. One method requires slicing the separation matrix and physically removing matrix fragments containing the subject species. Such matrix fragments are then processed on glass or Sephacryl S-300 columns, or electroeluted using buffer-filled dialysis bags, followed by concentration and purification. Alternatively, molecular species may be electrophoresed directly onto NA-45 paper, or another adsorption membrane, which may then be removed from the gel for further investigation of sample. (Current Protocols, supra)

Though electrophoresis is a well studied phenomena, researchers have not developed methods or apparatus for using electrophoresis in conjunction with recently developed miniature components for analyzing biomolecules. Small sized electrophoresis apparatus such as the 43×50× 0.45 mm gels of the PhastSystem of Pharmacia Biotech (Uppsala, Sweden) do not offer enough sensitivity for the micro-manipulation of tiny samples of charged molecules. Biosensors such as those disclosed in U.S. Pat. No. 5,063,081, U.S. Pat. No. 5,200,051, U.S. Pat. No. 5,212,050 and U.S. Pat. No. 5,112,455 granted to Cozzette et al., which are incorporated herein by reference, operate on the scale of a few square millimeters. Other researchers have developed tiny silicon wafers, related to computer chips in their appearance, that can be used for chemical and enzymatic manipulation of biomolecules. Miniature components that can be used for detection, measurement or modification of biomolecules are also found in the following patents and patent applications which are incorporated herein by reference: WO 93/22680; WO 93/09668; WO 92/10587; WO 92/10092; U.S. Pat. No. 5,384,261; U.S. Pat. No. 5,320,725; U.S. Pat. No. 5,286,364; U.S. Pat. No. 5,264,105; U.S. Pat. No. 5,264,104; U.S. Pat. No. 5,262,305; and U.S. Pat. No. 4,975,175.

An electrophoresis system which is capable of very small scale movement and separation of nucleic acids and other charged molecules could be extremely useful in conjunction with miniature components to accomplish rapid and cost effective diagnoses of medical conditions, to conduct complex experiments using tiny quantities of reagents, and to generally take advantage of the development of miniature bio-analytical and bio-manipulative components, such as those listed above.

It is an object of the instant invention to provide methods and apparatus for manipulation of a sample of biomolecules such as nucleic acids and other electrically charged molecules.

It is a further object of the instant invention to provide methods and apparatus for the movement and separation of samples of charged molecular species in a miniature electrophoresis apparatus.

It is a further object of the instant invention to provide a process for the fabrication of a miniature electrophoresis apparatus.

These and other objects of the invention are obtained according to the following specification

SUMMARY OF THE INVENTION

In accordance with the disclosure, the instant invention relates to a method and apparatus for moving and separating charged molecules such as nucleic acids, and to a separation matrix useful in use a method and apparatus. The instant disclosure also relates to processes for the fabrication of such a separation matrix, in the form of a small scale chip.

The separation matrix of the invention comprises a substrate in which there are formed one or more channels, one channel for each sample to be evaluated. The channels extend for the length of the chip, a distance of generally around 1 cm, and are about 1 to 10 Sun wide and 1 to 10 gm in depth. The channels are filled with a homogeneous separation matrix which acts as an obstacle to the electrophoretic migration of the charged molecules. Microelectrodes disposed in the channels are used to induce an electric filed within the homogeneous separation medium. When a voltage is applied across two or more of the microelectrodes, the charged molecules are induced to move and separate according to the electric field density, the type of solvent film, and the charge, shape and size of the charged molecule.

The separation matrix may further comprise detectors, such as light polarization detectors, fluorescence emission detectors, biosensors, electrochemical sensors or other microcomponents which may include sites for enzymatic or chemical manipulation of the moved or separated charged molecules.

When the apparatus is used in conjunction with a second substrate, substantially parallel to the first substrate, electrodes may be located on either or both substrates. The gap between the substrates is filled with the solvent film. Ultra-thin films on the order of 0.5–100 microns thickness, preferably 2–10 microns thickness are effective for rapid, energy efficient separations of nucleic acids and other charged molecules. Such arrangements may include sample loading and sample collection sites, as well as sites for enzymatic or chemical manipulation of the moved or separated charged molecules.

DETAILED DESCRIPTION OF THE INVENTION

According to the instant invention, charged molecules may be moved through a channel filled with a homogenous separation medium which acts as an obstacle to electrophoretic separation under electromotive force supplied by a series of micro-electrodes disposed on the substrate supporting the solvent film. The invention finds application in numerous fields, and particularly in the field of nucleic acid analysis.

It is well known in the art that negatively charged molecules such as nucleic acids in pH neutral solution migrate under an electric field towards the anode. Many commercial apparatus are available which use these techniques to separate proteins and nucleic acids by charge and size. The present invention uses the known principles of electrophoresis in a novel fashion, by employing an extended series of micro-electrodes to move a sample, e.g., a nucleic acid sample, through a homogeneous separation medium to a desired location for detection or further reaction.

Figure 1A:
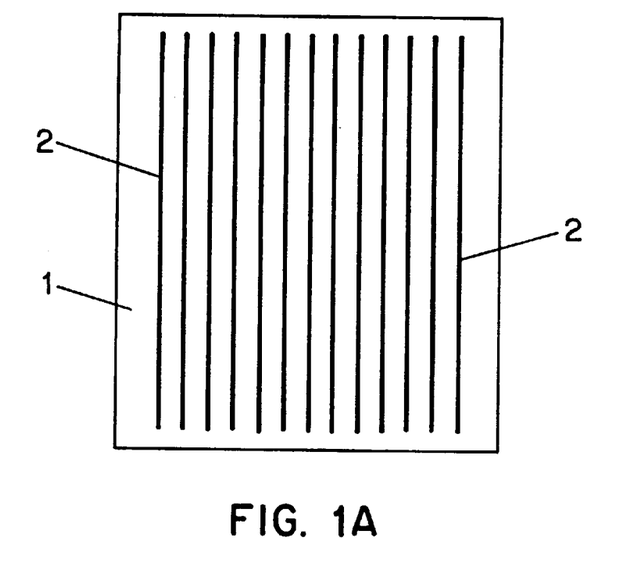
FIGS. 1A and 1B show a separation matrix according to the present invention.
Figure 1B:
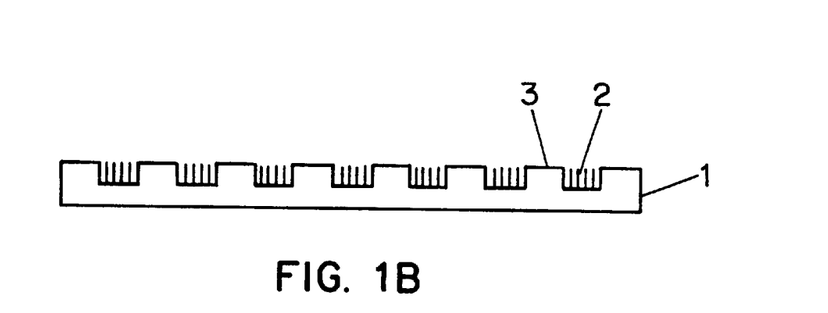

FIG. 1A shows a separation matrix according to the present invention. As shown, the separation matrix has a solid support 1 on which are disposed a plurality of channels 2. In the embodiment shown in FIG. 1A, each channel 2 is approximately 10 μm wide and 1 to 10 μm deep, and is separated from neighboring channels by a separator 3 of approximately 10 μm in width. (FIG. 1B) The width of each channels is a matter of design choice and is not critical to the invention, although it will be appreciated, however, that the sizes noted above provide for the possibility of 50 channels in a 1 cm wide chip, which allows for very high throughput in a small area.

Figure 2A:
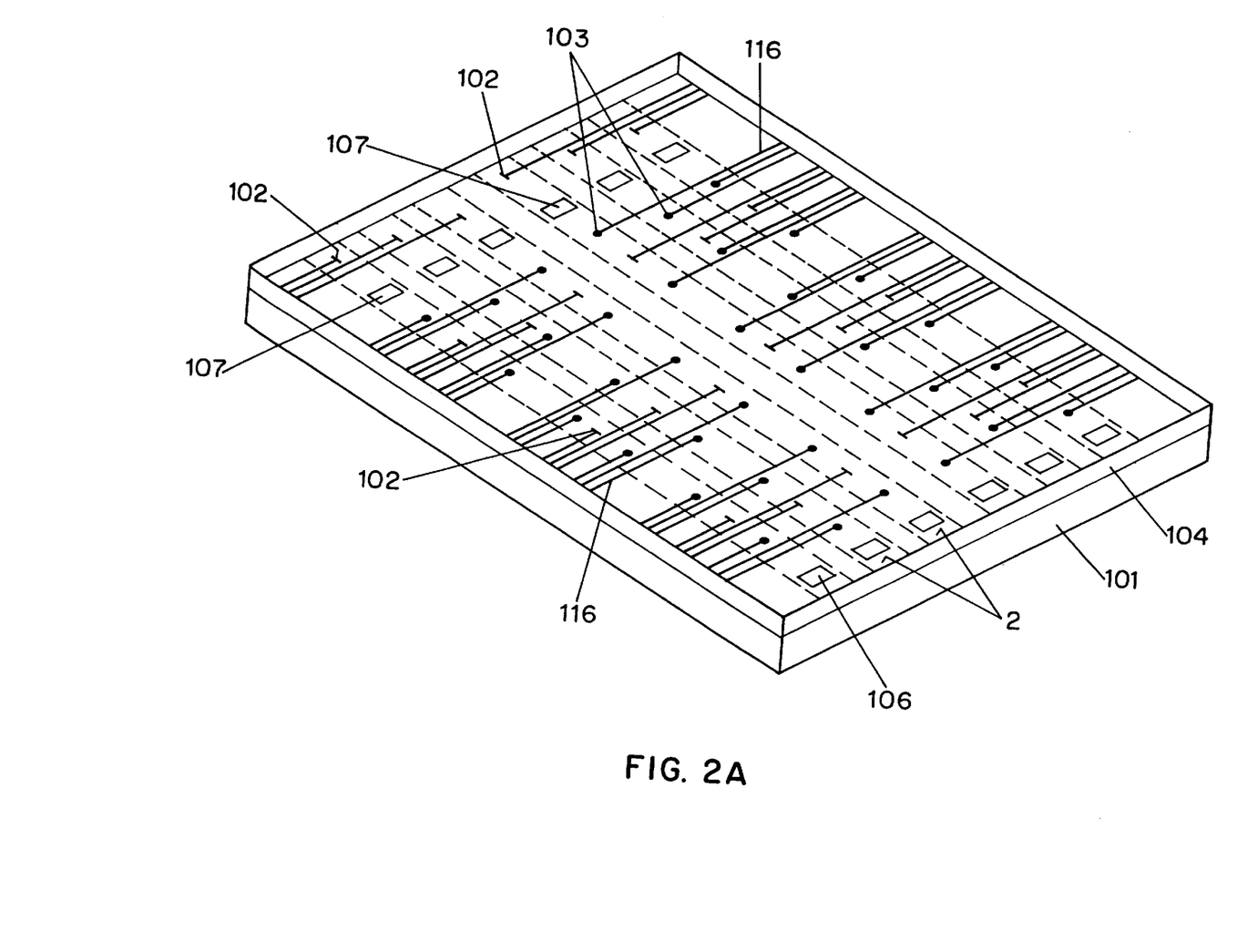
FIGS. 2A and 2B show an electrode layout for a separation matrix in accordance with the invention.
Figure 2B:
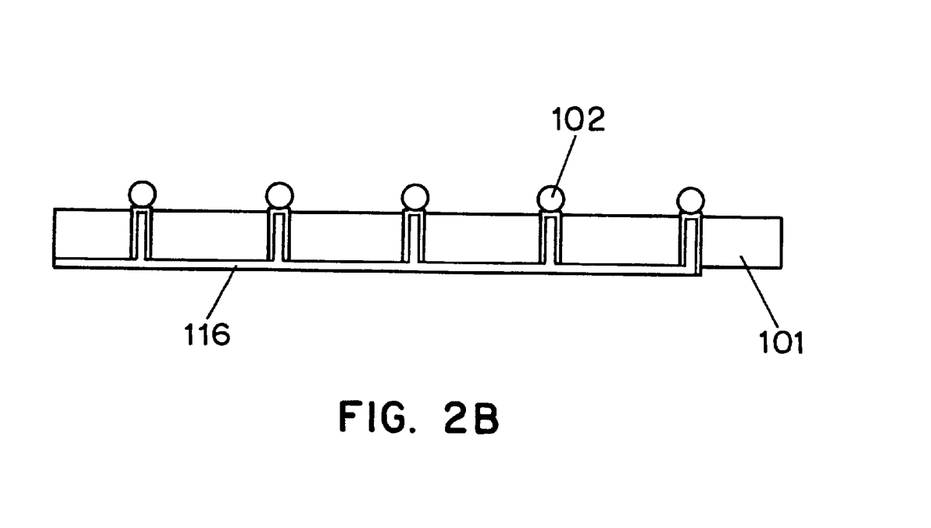

Within each channel a plurality of electrodes are formed, including at least on anode and one cathode. Preferably multiple anodes and cathodes will be formed in each channel to permit greater control of the electrophdretic process. FIG. 2A is a top view of a multi-channel device in accordance with the invention, with the channels shown in dashed lines for clarity. Within each channel 2 on substrate 101 there are a plurality of microcathodes 102, and a plurality of microanodes 103 (collectively the micro-electrodes). Leads 116 may run under the substrate 101 to connect to each microelectrode through microholes cut in the substrate as shown in FIG. 2B. Alternatively, leads may be formed in the bottom of the channel extending to the top and bottom edges of the chip.

Numerous methods of forming patterned microelectrodes and connecting wires on a substrate are known in the art, particularly in the art of integrated circuit production and LCD fabrication. Such methods include masking and vacuum deposition, silk-screening or stenciling, photolithography, chemical or machine etching and the like. The semiconductor industry uses electron resist or photoresists made from materials such as polymethyl methacrylate (PMMA) and its derivatives, and electron beam resists such as poly(olefin sulfones) and the like (more fully described in Ghandi, "VLSI Fabrication Principles" Wiley (1983) Chapter 10, incorporated herein by reference) to produce the patterned micro-electrodes and connecting wires.

On top of the electrodes, each channel is filled with a homogeneous separation medium which acts as an obstacle to the migration of the charged molecules, and in particular to the migration of polynucleotide fragments produced in a sequencing reaction. The homogeneous separation medium will contain a liquid carrier, generally water optionally including a cosolvent, appropriate buffers and salts to inhibit DNA annealing, and materials which function as obstacles to migration. In general, the homogeneous separation medium will be a colloidal or colloid-like suspension containing homogeneously sized and distributed structures having a size on the same order as the gyration radius of the polymers to be separated,, i.e., from about 0.5 to about 5 times the gyration radius. The separation medium should also be compatible with the detection system used. Thus, for fluorescence detection the separation medium should be transparent or translucent, with little or no fluorescence at the wavelengths of interest. Materials which can be used as obstacles in the homogeneous separation medium include monodisperse microspheres as described by Hosaka et al, *Polym. Int.* 30: 505–511 (1993) and Sanghvi et al, *J. Microencaps.* 10: 181–194 (1993), watersoluble fullerenes (C60) as described in Diederich et al., *Science* 271: 317–323 (1996), and self-assembling dendrimers as described in Newkome et al, *J. Org. Chem.* 58: 3123 (1993) and Zimmerman et al., *Science* 271: 1095–1098 (1996).

The substrate, 101, can be any non-conducting or low-conductance material such as glass, certain organic polymers, ceramics, silicon, germanium and the like. The substrate may also be formed of a combination of materials, for example ridges of a polymeric material such as polymethylmethacrylate disposed on a glass substrate. The substrate selected will depend on the fabrication method, described further below.

The micro-electrodes, 102 and 103 may be compositions of any relatively high conductance materials. Preferably the electrodes will be made of a coated or corrosion resistant material such as the noble metals platinum or gold. Corrosion resistance is required to withstand some highly reductive electrolytes which may be employed in the homogeneous separation media used with the device. Noble metals are not necessary is the device is disposable. Leads that are exposed to the solvent film must also have the same corrosion resistance of the electrode materials. Leads 116 that are not exposed to the solvent film can be made from less robust materials, such as indium tin oxide.

In order to prevent evaporation from the homogeneous separation medium or interference by airborne particles, the device of the invention may be covered by a protective sheet (not shown) made of a suitable non-electrically conducting material such as glass, a polymer or the like.

To use the chip shown in FIG. 2, sample is loaded into each channel at loading sites 106. An electric field is generated between the electrodes 102, 103 causing charged molecules in the sample migrate within the channel to a detection site 107. The loading site 106 may be located anywhere on the device, but is preferably located towards one edge of the micro-electrode array in order to take advantage of the separation characteristics of the device. In FIG. 2, the loading site is positioned such that the charged molecule may be drawn from the loading site into the array of electric sub-fields within each channel.

The pattern of the micro-electrodes on the substrate may be chosen according to the demands of the application for which the invention is employed. Two types of patterns are generally available. The first, illustrated in FIG. 2 is a spatially dispersed array in which each micro-electrode can be activated separately. Thus, electrodes which are required for a certain application may be turned on, while unnecessary ones may simply be turned off. The second option, is a dedicated pattern which is employed for applications where known separation distances and voltages are available. In this case, the electrodes can be laid out in a fixed pattern which is known to be satisfactory for the desired application. A 0.1 mm to 10 mm, preferably about 1 mm, separation between micro-electrodes is useful for the applications of the invention.

Not shown in FIG. 2 is a temperature control device that may be desirable for certain applications. The substrate may be temperature-controlled using a device such as a Peltier device, a water bath, air circulation or other means.

The substrate having channels formed therein can be formed using any of a variety of methods. Thus, microscopic grooves can be cut or etched into a substrate to define the channels. Because it is desirable to make the chips of the invention at low cost, however, repetitive molding techniques are preferably employed.

Separation matrices according to the invention can be manufactured using ultraviolet lithography to form a mold which is the reverse of the desired pattern channels and separators, casting the substrate in the mold, and then optionally fusing the cast substrate to a solid support for stripping from the mold. Preferably, the mold is reusable.

To form the mold, a substrate is coated with a pattern receiving layer or layers. For example, as shown schematically in FIG. 3, a tungsten substrate 31 which will ultimately form the mold, may be coated with a thin layer of a dielectric such as silicon dioxide 32, a thin layer of a low cross-section, highly conductive metal, such as aluminum 33, and a layer of an ultraviolet light sensitive resist 34. The resist layer may be deposited by spray deposition or through the formation of a Langmuir/Blodgett film on water, followed by transfer to a solid surface. Miyashita et al., *Prog. Polymer Sci.* 18: 263–294 (1993).

Figure 3:
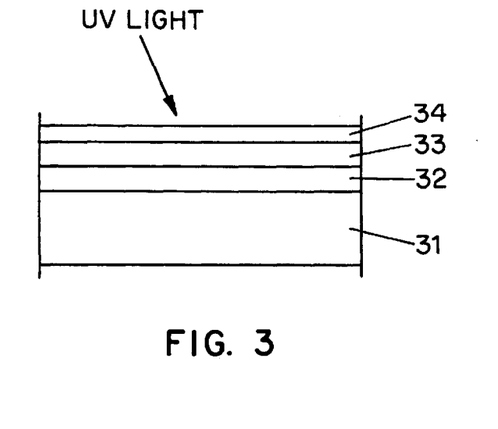
FIG. 3 shows a layered composite useful for forming a mold to make the separation matrix of the invention.

The coated substrate is positioned on the stage of a lithography tool having appropriate resolution to draw lines of the dimensions desired. The ultraviolet light beam is used to write a pattern in the resist which is either a positive image (in the case of a positive resist which hardens to resist removal when exposed to the electron beam) or a negative image (in the case of a negative resist which becomes removable when exposed to the electron beam) of the posts and pores of the desired obstacle course. The exposed resist is then developed, to leave the patterned mask on the substrate. Preferred resists are positive resists such as polymethylmethacrylate derivatives, since these will in general provide the highest resolution. Cowie, J. M. G., *Polymers: Chemistry and Physics of Modern Materials.* 2nd ed. Blackie, London, (1991).

Once the pattern has been formed, the next step is the transfer of the pattern down through the layers of the substrate using successive treatments with specific chemical etchants, culminating in the etching of the substrate itself to produce a reusable mold for use in forming the separation matrix of the invention.

The substrate having the channels formed therein can be made of any of a number of materials, and the manner of forming the matrix within the mold will depend to a large extent on the nature of the material selected. For example, separation matrices made from silicon dioxide or similar materials can be formed using a chemical vapor deposition process to deposit material within the mold. Thereafter a glass base can be fused to the deposited materials, for example using the technique of field assisted silicon glass fusion (Wallis et al., *J. Appl. Phys.* 40: 3946–3949 (1969)) to increase the dimensional stability of the molded matrix and to facilitate its separation from the mold.

The matrix may also be formed from a variety of polymeric materials, including polymethylmethacrylate, ultraviolet-curable polyurethanes, ultraviolet-curable epoxies and other polymers with suitable physical and chemical properties, i.e., optical transparency and low fluorescence at relevant wavelengths, thermal conductivity and lack of electric charge. These materials can be formed into the channels and separators relying on capillarity as in the techniques of polymer casting (Kim et al, *Nature* 376: 581–584 (1995), and then cured either chemically or photochemincally.

A mold as described above can also be used to form the separation matrix of the invention using the technique of imprint lithography as described by Chou et al., *Science* 272: 85–87 (1996). In this technique, a thin layer of a polymer resist such as polymethylmethacrylate is applied to a substrate. The polymer resist is then softened to a gel by heating it to a temperature above its glass transition temperature, and the mold is pressed against the softened resist to form a thickness contrast pattern. The mold is then removed and an anisotropic etching process such as reactive ion etching or wet etching is used to remove the resist from the compressed areas.

Figure 4:
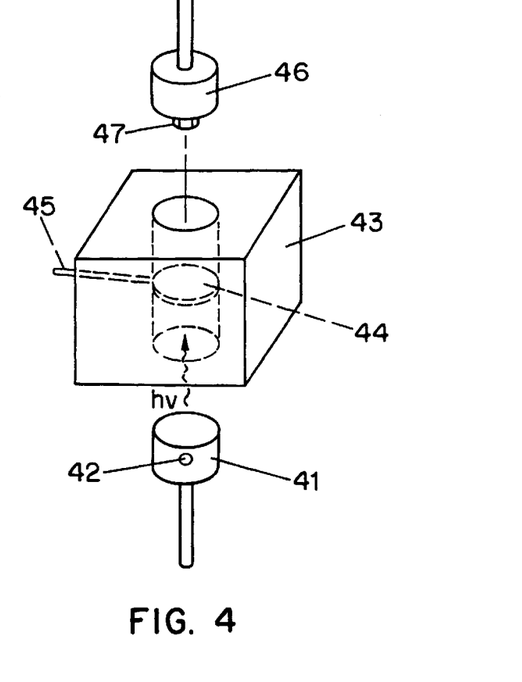
FIG. 4 shows an apparatus for manufacturing separation matrices.

FIG. 4 shows an apparatus suitable for forming multiple replicate copies of a DNA sequencing chip, using a mold and a photopolymerizable material using the procedures discussed above. As shown, a moveable base 41 having a lamp 42 for delivering light suitable for inducing photopolymerization positioned therein is disposed within a housing 43. The base 41 supports a chemically treated glass cover slip or other substrate 44 in alignment with an injection port 45 in the housing. Monomer or prepolymer solution is injected through the injection port 45 onto the top of the substrate 44. A piston 46 having the mold 47 for the pattern of plugs and pores is then pressed down into the solution on top of the substrate 44. The lamp 42 is then turned on to polymerize the solution in the mold, after which the molded polymer is separated from the mold 47 and the housing 43 by raising the piston 46 and lowering the base 41.

A modified version of the device of FIG. 4 could instead be used to repetitively make multiple copies of a DNA sequencing chip by imprint lithography. In this case, instead of a monomer or prepolymer solution, a polymeric sheet would be used as the starting materials. This would be heated above the glass transition temperature and then piston 46 having mold 47 would be pressed down into the softened polymeric sheet to make the replica. The temperature would be lowered again below the glass transition point and then piston 46 and mold 47 would be removed. Instead of lamp 42, this apparatus would have a heating element.

Figure 5:
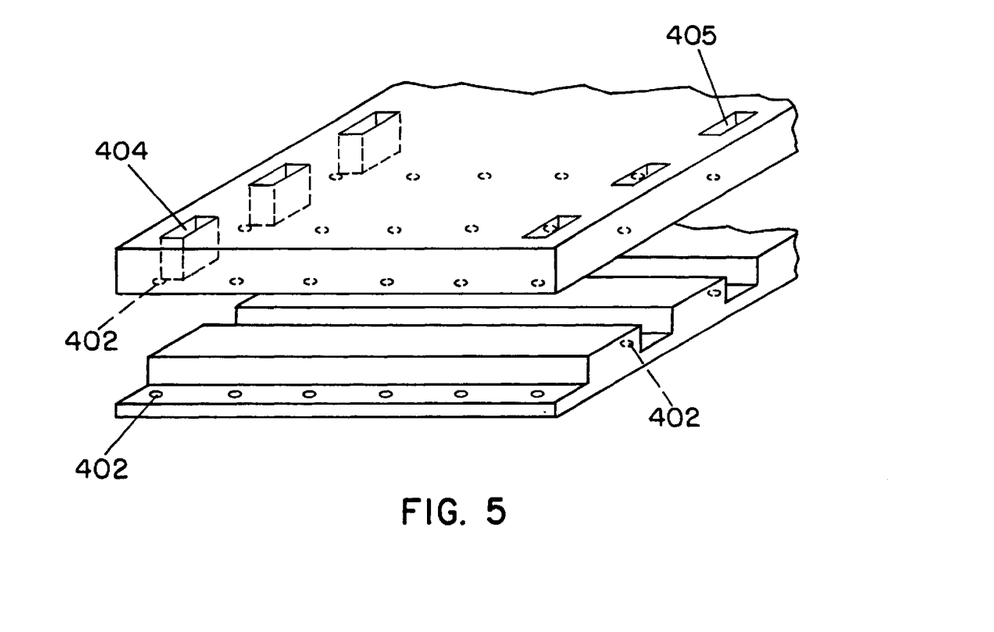
FIG. 5 shows a chip in accordance with the invention having a top and bottom substrate.

FIG. 5 illustrates the use of two substrates, 401, for the generation of a micro-electrophoresis chip. The construction of the chip is basically the same as for the single substrate chip, except that only one of the two substrates needs to have channels formed therein. Micro-electrodes, 402, are patterned on each chip, in mirror image arrays, such that when electrode supporting faces are opposed, electrodes are disposed directly across from one-another. In two-substrate chips, the facing substrates should be exquisitely aligned in opposition to each other in order to generate the correct electric field distribution in the gel matrix when switched on. Methods for fixing chips in this fashion using adhesive containing glass spacer beads are disclosed in U.S. patent application Ser. No. 08/332,577 which is incorporated herein by reference. Methods for filling the gap, 403, between substrates with a separation matrix are disclosed in U.S. patent application Ser. No. 08/332,892 which is incorporated herein by reference. Loading, 404, and collection/detection sites, 405, may be cut into one of the substrates for sample manipulation.

Loading of samples in accordance with the invention may be performed using a micropipettor. For some applications, however, the desired sample volume may be smaller than can be reproducibly dispensed in this manner. In this case, a special loader which concentrates the sample prior to loading it on the separation matrix may be employed. Such a loader is shown in FIG. 6.

Figure 6:
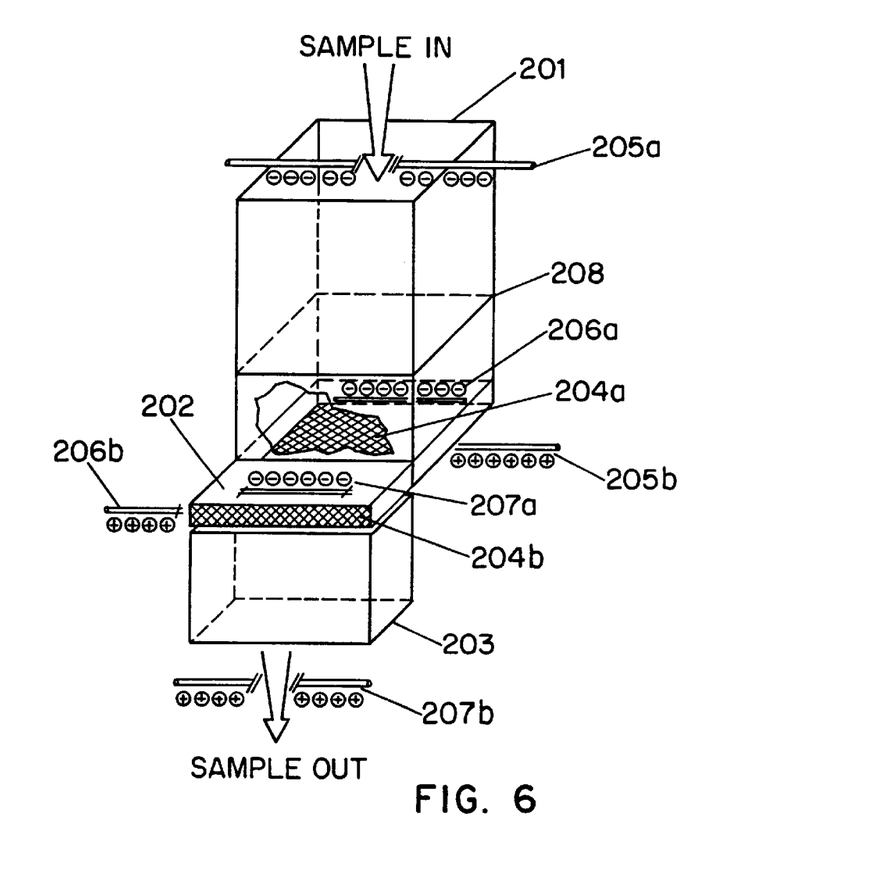
FIG. 6 shows a sample concentrating and loading device.

The device of FIG. 6 is shown in an orientation appropriate for loading sample into a channel of a DNA sequencing chip 203 that is in the vertical orientation. The loader consists of a large rectangular channel 201 attached at right angles to a second smaller rectangular channel 202. The upper face of the large rectangular channel 201 is open, and receives a volume (for example 100 nL of unconcentrated sample containing a DNA mixture to be separated. The lower face The lower face of the smaller rectangular channel 202 is also open and releases the concentrated sample (approx 1 pL) into one of the functional channels of the DNA sequencing chip 203. There is an unrestricted passageway between the large and small channels, to allow sample to flow between them, at a time after a first concentration step and before a second concentration step.

In the first concentration step, sample loaded into the top of the large channel 202 is electrophoresed using a filed generated between electrodes 205a and 205b. The DNA is collected on a semipermeable membrane 204a which has a molecular weight cutoff low enough to prevent passage of the DNA but which permits passage of the solvent from the sample, thereby effecting a first concentration of the sample on the semi-permeable membrane 204a.

Next, a second set of electrodes 206a and 206b are turned on to generate cause the concentrated sample to migrate in a direction perpendicular to the original migration from the semi permeable membrane 204a into the small channel 202. A second semipermeable membrane 204b retains sample within the small channel 202 while permitting passage of solvent. Finally, a third electrode set 207a and 207b is used to electrophorese the doubly concentrated sample from the small channel 202 into one of the functional channels of the DNA sequencing chip 203.

If is also possible by means of thermocouple strips 208 disposed about the periphery of the large channel 201 to achieve localized cooling of buffer in the large channel, via the Peltier effect. This strategy can be used to lower the temperature of a glycerol-containing buffer below the glass-transition temperature, thus creating a viscosity trap close to the semipermeable membrane 204a which prevents back-diffusion of concentrated DNA in the vertical direction within the large channel after the first concentration step.

It is also possible to use a simplified version of the device of FIG. 6, in which only a single stacking operation is employed. This simplified device consists of channel 201, semipermeable membrane 204a, electrode sets 205a and 205b, and 206a and 206b, and optionally the Peltier strips 208. Electrode set 206a and 206b causes the concentrated sample to be electrophoresed directly into a DNA sequencing chip rather than into a second concentration channel.

The processes that occur during the loading operation can be summarized as follows: (1) electrophoresis along the z-dimension onto a semipermeable membrane; (2) optional trapping of sample close to the membrane with a "viscosity trap"; (3) electrophoresis in the x-direction into a second semipermeable membrane; and electrophoresis in the z-direction into a functional channel in the DNA sequencing chip.

The degree of sample concentration that can be achieved in either of the stacking steps can be calculated from the theory of equilibrium electrophoresis using the equation:

$$C(z)=C_0 e^{\sigma(z-z_0)-2B[C(z)-C_0]}$$

where $C_0$=concentration at arbitrary reference distance ($z_0$) along the electrophoretic direction, B=second virial coefficient, and $\sigma=E \cdot [\psi/k_B T]$ where E=electric field strength (V/cm), $\psi$=apparent or effective net charge (Coulombs), $k_B$=Boltzmann's constant, and T=absolute temperature. It is apparent from this equation that an arbitrarily large degree of stacking or concentration can be achieved simply by raising the electric filed strength to a sufficiently high value.

In the most general application, the present invention is used to move and/or separate species of charged molecules, and in particular charged bio-molecules such as proteins and nucleic acids. Further, the instant invention may be used to purify one molecular species from a sample of mixed molecular species.

The object of combining the homogeneous separation matrix with closely positioned electrodes is the creation of localized very-high density electric fields in the separation matrix. These localized fields can be supported with very low energy power supplies, and are therefore energy efficient. U.S. patent application Ser. No. 08/332,577, which is incorporated herein by reference, demonstrates the usefulness of high density electric fields for separating charged molecules such as nucleic acids and proteins. Nucleic acids separated under extremely high electric fields (100–400 V/cm) over localized areas (1–5 mm²) can be detected and/or used by conventional detectors, biosensors and micro-reactor components. These miniature components may be located at one site, or more than one site on the device, as illustrated by reference number 107, FIG. 2A.

Many types of conventional detectors, biosensors and micro-reactor components may be employed with the instant invention. Each of these devices are described below. For detecting fluorescently labeled materials of the type commonly used in the DNA sequencing reactions, various types of illumination and detection can be used, including:

(i) Diode laser illuminator and fibre optic/phototransistor detector (Sepaniak et al., *J. Microcol. Separations* 1: 155–157 (1981); Foret et al., *Electrophoresis* 7: 430–432 (1986); Hirokawa et al., *J. Chromatography* 463: 39–49 (1989); U.S. Pat. No. 5,302,272).

(ii) Array of diode-laser illuminators and two-dimensional CCD detector. The design for a two-dimensional CCD array detector has been described elsewhere (U.S. Pat. Nos. 4,874,492 and 5,061,067 which are incorporated herein by reference, Eggers et al., *BioTechniques* 17: 516–524 (1994); Lamture et al., *Nucleic Acids Res.* 22: 2121–2125 (1994)). Such a system is advantageously constituted as a fixed array, into which a boardmounted DNA sequencing chip is inserted. This separates the mass-produced and relatively inexpensive sequencing chip from the expensive detection system.

(iii) Epifluorescence Microscope and Image Intensifying Camera.

Figure 7:
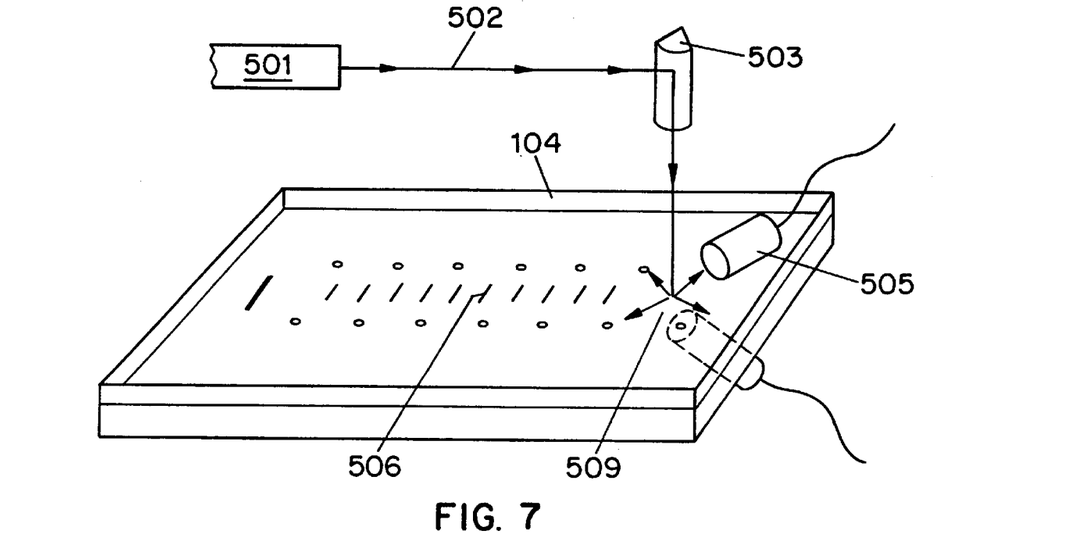
FIG. 7 shows a fluorescence detection embodiment of the instant invention.

FIG. 7 shows a fluorescence detection embodiment of the instant invention. A radiation source 501 which provides radiation 502 sufficient to cause a conjugated label fluorophore such as fluorescein to fluoresce, is disposed, with the use of a directing mirror 503, so as to illuminate a detection site on the chip 504. The detector 505 is positioned to detect the passage of a charged molecule 506 as it passes through the detection site 504, and emits fluorescent radiation. The detector 505 may be disposed to receive fluorescence emitted towards the top side of the chip, or, the detector may be positioned below the chip 507 if the substrate transmits the fluorescent radiation. A plurality of detectors may be positioned so as to receive fluorescence emissions from different parts of the chip. Alternatively, one detector may be disposed so as to translationally move with respect to the substrate and thereby detect charged molecules at a plurality of locations (not shown).

While fluorescence detection is the most common technique currently employed in analysis of DNA sequencing fragments, and thus is a preferred approach in the present invention, other detector types can be used. For example, a subject molecule labeled with a radioactive moiety may be detected with a radiation detector, such as X-Ray film or a scintillation counter. Unmodified nucleic acids may also be detected by shifting polarization of input radiation as disclosed in U.S. patent application Ser. No. 08/387,272, which application is incorporated herein by reference.

Other types of detectors may also be employed in the chip of the invention to provide information about the presence or nature of a separated material. Electronic detectors that may be used include any device that electronically measures the changes in conductivity, resistance, pH, charge density or dielectric constant of a detection site in the solvent film. The main issue in the selection of the electronic detector, as with optical and radioactive detectors, is whether the sensitivity of the detector is sufficient to detect the passage of the charged molecule through the solvent film.

Transistors which permit or prevent current flow between electrodes when charged species pass between the electrodes are most advantageous for they permit instantaneous "digital" analysis of species of charge carrying molecules that are separating in the electrophoresis separation matrix.

Biosensors that may be used with the invention include any of those biosensors which detect very small amounts of analytes. For example, the enzyme electrodes disclosed by Gregg, Heller et al. in U.S. Pat. Nos. 5,264,105, 5,264,104 and 5,320,725, which are incorporated herein by reference, disclose an improved enzyme electrode, wherein a three-dimensional redox polymer network having redox enzymes bound to the network is closely associated with an amperometric electrode. When the substrate for the enzyme is present, a metabolite produced changes the current detected by the electrode. An enzyme electrode which reacts with nucleic acids is a suitable biosensor for use with the instant invention.

Other miniaturized biosensors which may be advantageously employed with the present invention include U.S. Pat. No. 4,975,175, incorporated herein by reference, which discloses a miniaturized electrode disposed in a solvent polymer wherein immobilized biological substances such as a microorganism, an enzyme or a mixture of enzymes produce analytes which are detected by the electrode. Analytes are the metabolized products of the compound for which the test is desired. U.S. Pat. No. 5,286,364 granted to Yacynych et al. and incorporated herein by reference discloses an electrode for a biosensor with an enzyme immobilized in a polymer layer. The enzyme produces an analyte which is detected by the electrode. U.S. Pat. No. 5,262,305 granted to Heller and Maidan and incorporated herein by reference discloses a miniature biosensor with an interferant-eliminating catalyst for analyzing an analyte in a biological sample.

While biosensors simply detect the presence or absence of an analyte, miniature bioreactors, wherein the charged molecular species is usefully modified, can also be integrated into the micro-electrode array of the instant invention. For example, the very large scale immobilized polymer arrays disclosed in WO 92/10092 and U.S. Pat. No. 5,384,261, which are incorporated herein by reference could be located at the sites, 107, of FIG. 2A. One of the principal uses for such polymer arrays is for hybridizing DNA fragments, to determine nucleotide sequence. Thus, in combination with the instant invention, a single fragment isolated from a stream of fragments can be sequenced. This is useful for HLA or microsatellite analysis wherein fragments from many different genes are amplified.

The researcher may want confirmation of the nature of the fragment isolated. The fragment is then drawn by microelectrodes in a second direction, into the reaction pool for hybridization. The successfully hybridizing oligonucleotide can thereafter be used to determine the sequence of the subject fragment, or identification may be based on the fact that hybridization occurred.

Having described the features of the invention, the following examples are disclosed in order to further describe use of the invention, and are not meant to limit the instant invention.

EXAMPLE 1

Figure 8A:
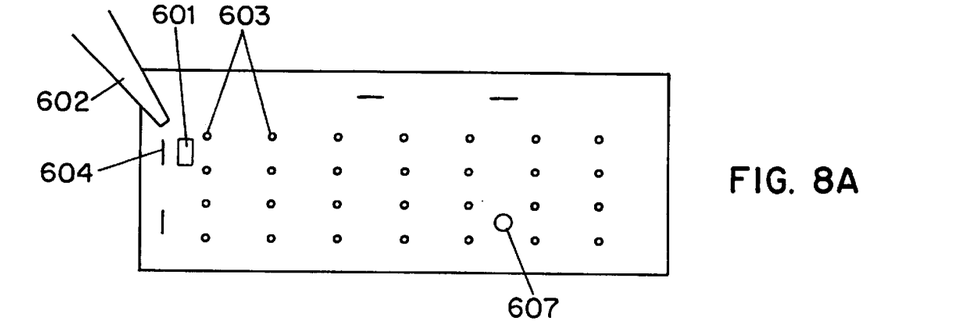
FIGS. 8A–8E shows a particular use of the chip of the invention.
Figures 8B, 8C:
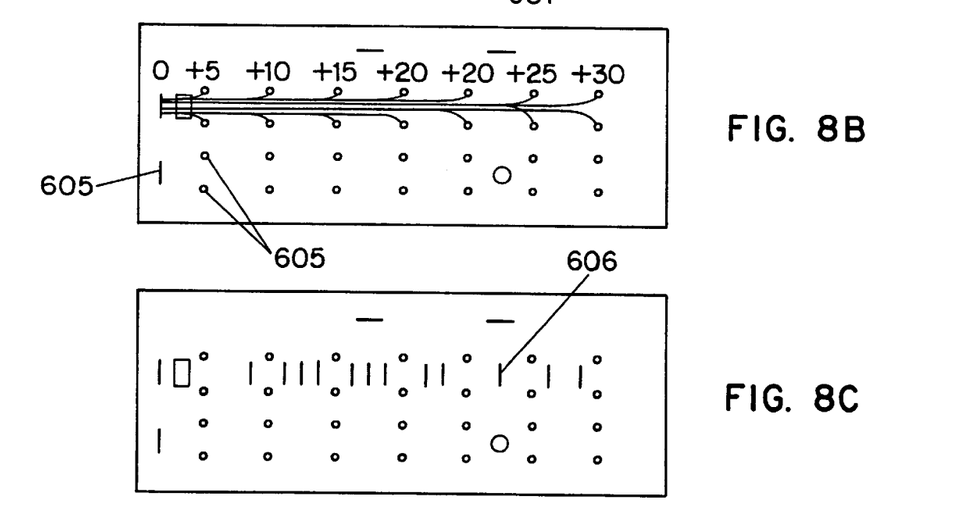
Figure 8D:
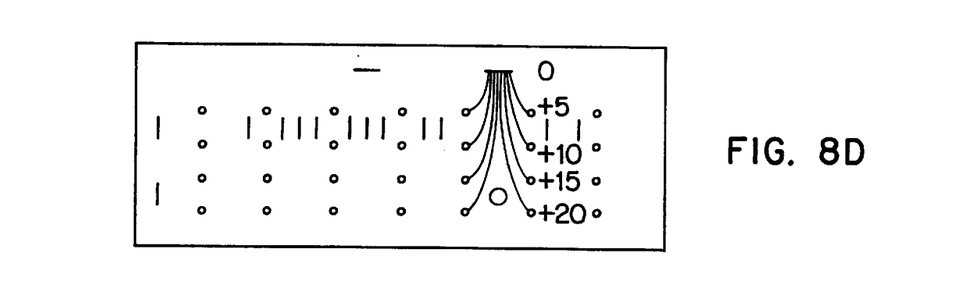
Figure 8E:
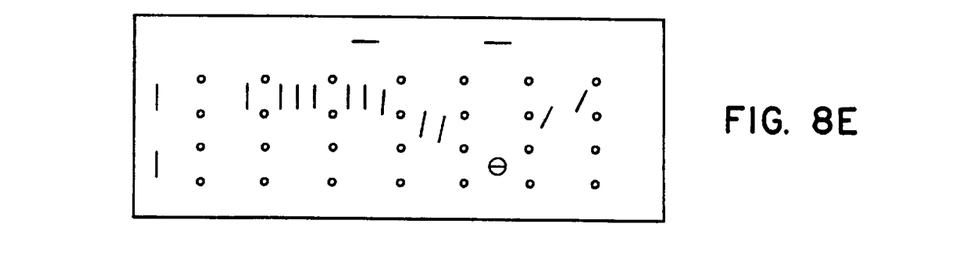

FIGS. 8A–8E shows a particular use of the invention when a wide channel (for example 40–100 $\mu$m wide) is used. 8A) A sample containing the charged molecule of interest is placed or "loaded" into the separation matrix at the loading site, 601, using a capillary pipette, 602. 8B) The electric field of the apparatus is induced by applying a voltage between selected micro-anodes, 603 and a selected micro-cathodes, 604. Other electrodes, 605, are not activated at this time. The sample begins to migrate in a first direction. 8C) Once the fragment of interest, 606, is sufficiently separated from the other species, the electric field is turned off. 8D) Next, an electric field is induced in a second direction that is located so as to draw the separated species of interest into a collection site, 607. The separated species, 606, migrates as a single band to the collection site. Other molecular species are not drawn to the collection site at the same rate as the fragment of interest, 607. When the fragment of interest. 607, reaches the collection site, 606. the electric field is switched off. In this way, a single nucleotide species be separated from a sample of mixed species. (FIG. 8E)

EXAMPLE 2

Figure 9A:
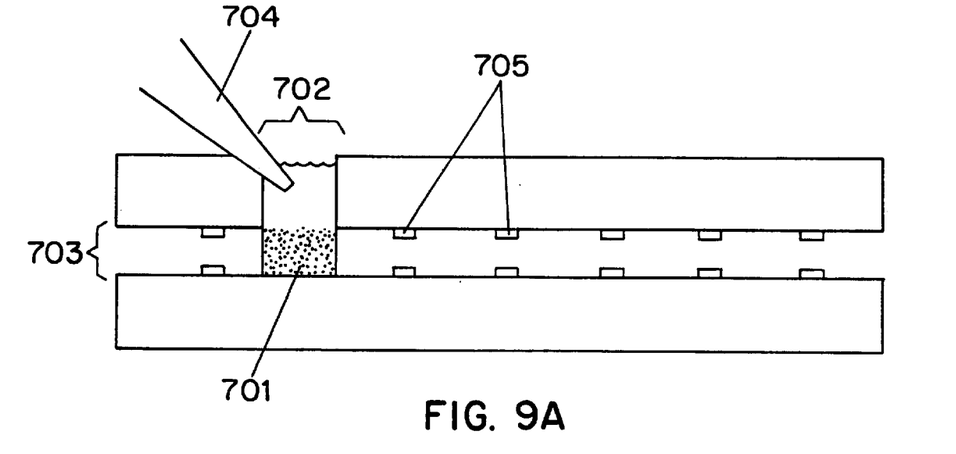
FIGS. 9A–9C show a particualr use of the chip of the invention.
Figure 9B:
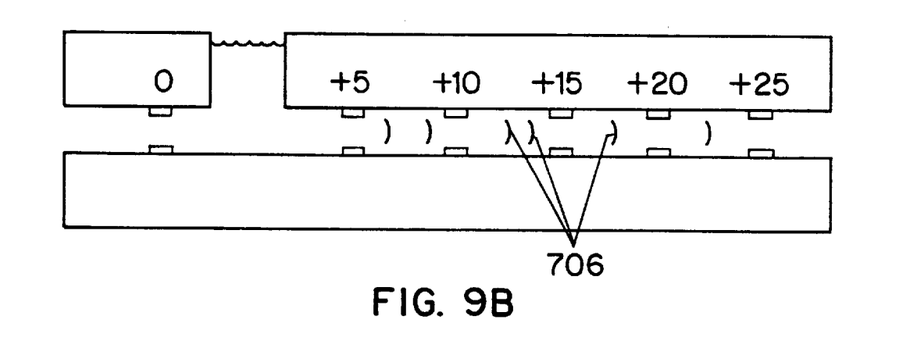
Figure 9C:
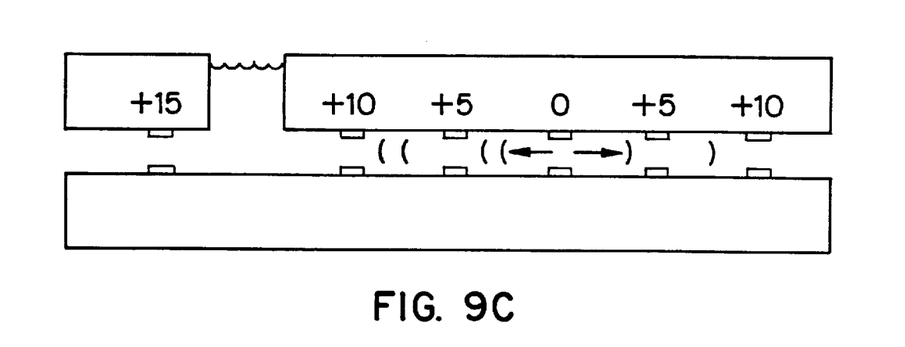

In a two substrate system, small nucleotide fragments are separated from large fragments by switching the charges on electrodes during the course of electrophoresis. In FIGS. 9A–9C, the sample, 701, is loaded through the loading site, 702, into the separation matrix, 703, by a capillary pipettor, 704. As it is in a horizontal format, the loading site is gently topped up with buffer after the sample is loaded. Electrophoresis begins with the voltages between micro-electrodes, 705, as shown in FIG. 9A. After a short period of time, FIG. 9B, the sample separates into species, 706, with the smallest fragments moving the fastest, and electrophoresis is stopped. When electrophoresis restarts, FIG. 9C, the voltages across the electrodes are changed, such that fragments on one side of a break point, 708, are drawn in one direction, while fragments on the other side are drawn in another direction, as indicated by the arrows. An apparatus as noted may require a detector (not shown) to determine where and when separation has been achieved. Ultimately, fragments on either side of the break point, 708, may be drawn to separate locations on the thin film micro-electrophoresis chip.

EXAMPLE 3

Figure 10:
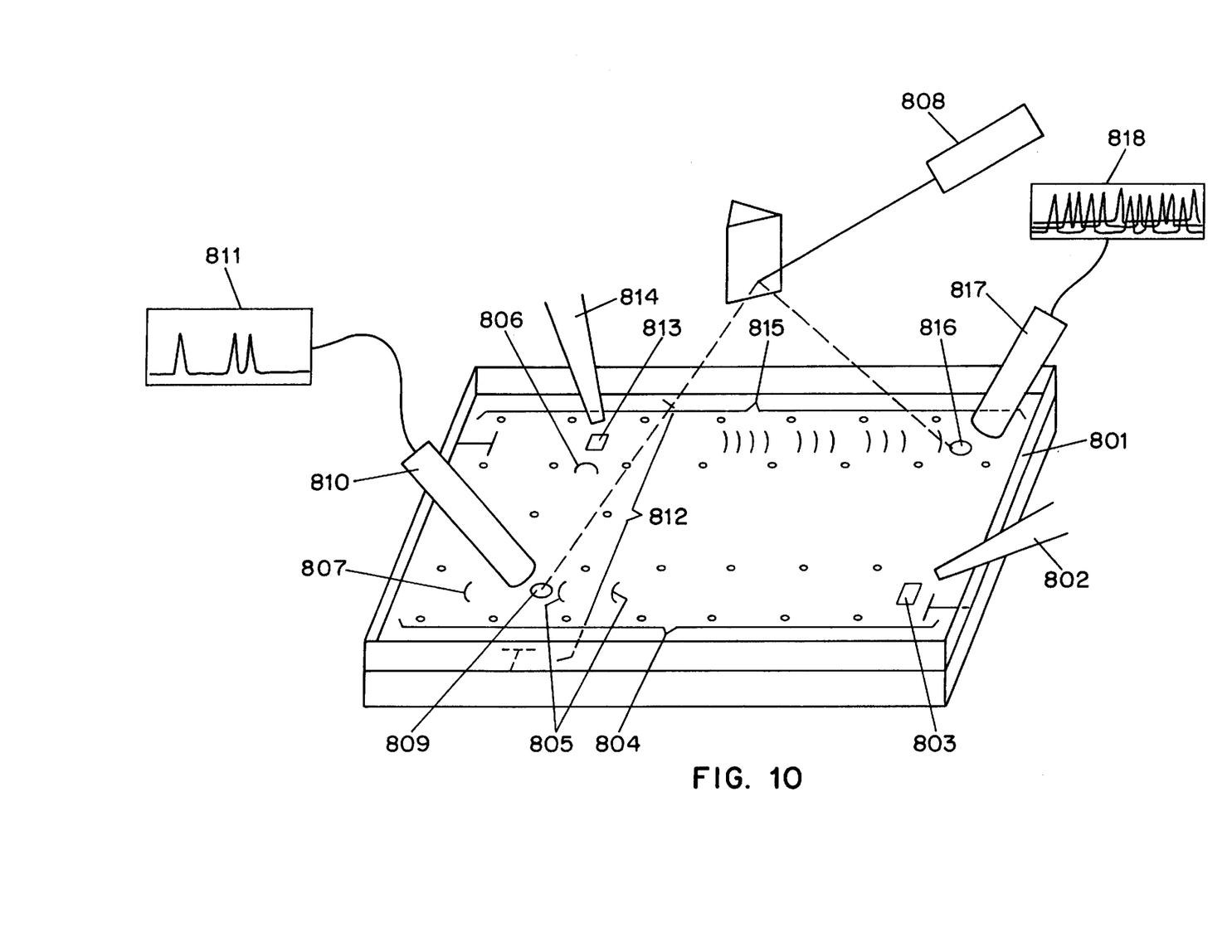
FIG. 10 shows a layout of an integrated DNA diagnostic chip in accordance with the invention.

A further advantage of the instant invention, is the ability to move samples from one well to another for different treatments, such as in an integrated DNA diagnostic chip. As described in U.S. patent applications Ser. Nos. 08/271,946 and 08/271,942 which are incorporated herein by reference, the most cost effective means of DNA diagnosis involves a hierarchical method of testing, wherein a series of analyses of increasing accuracy are employed to diagnose the presence or absence of genetic mutation. It is possible to integrate all the hierarchical steps on one chip, as illustrated in FIG. 10. FIG. 10 shows an integrated DNA diagnostic chip which uses the diagnostic method of the above noted patent application. A highly simplified discussion of the steps involved in the hierarchical method is provided below. In the first step, a group of exons of a gene to be diagnosed is examined for insertion and deletion mutations. In a reaction tube (not shown) the suspect exons of the patient are amplified by multiplexed PCR using oligonucleotide primers labeled with a fluorophore (not shown). The resulting fragments of DNA are loaded into the separation matrix, 801, with a capillary pipettor, 802, at loading site, 803. Upon activating a group of microelectrodes, 804, the sample will migrate through the separation matrix, 801, and resolve into discrete bands of distinct species, 805, 806 and 807. A laser source, 808, of a wavelength suitable to excite the fluorophore is directed to an excitation site, 809. As a band, 806, passes through the excitation site, 809, its fluorescence emissions are detected by detector 810. The fluorescence emissions may be recorded or displayed, 811. If the band has an insertion or deletion relative to the normal gene, it will pass through the excitation zone at a time different from the expected time. Such a difference indicates the presence of a mutation in that fragment. The difference can be directly reported to the patient file. If, however, no insertion or deletion mutation is found, it is then necessary to turn to the second step of the diagnostic method, and determine the actual sequence of the DNA to determine the presence or absence of point mutations. To achieve this objective, a separated DNA fragment is moved, according to the method of the instant invention, by a series of micro-electrodes, 812 to a reaction center, 813.

Immobilized enzymes such as DNA sequencing enzymes may be located at reaction pools, as described in U.S. Pat. Nos. 4,975,175 and 5,286,364, which are incorporated herein by reference. When provided with proper reagents, which may be added by a second capillary pipettor, 814, the sequencing reaction may be carried out in situ on the diagnostic chip. After a suitable length of time, the reaction is completed. The sequenced DNA sample is then separated in a third direction by the activation of a third group of micro-electrodes, 815. DNA sequence is obtained according to conventional fluorescence DNA sequencing: The laser source, 808, is directed to the excitation site, 816. Fluorescence emissions of the sample are recorded by a detector, 817 and recorded or displayed 818. The presence or absence of point mutations is then recorded and reported to the patient file.

EXAMPLE 4

Research has shown that DNA, like other semi-rigid polymers in high concentration, has a natural tendency to form a liquid crystal at approximately 250 mg/ml. (Strzelecka TE; Davidson MW; Rill RL; Multiple liquid crystal phases of DNA at high concentration; Nature 1988; 331: 457–60; Rill RL; Liquid crystalline phase in concentrated aqueous solutions of Na+DNA. Proc. Natl. Acad. Sci. USA 1986; 83(2) 342–6). An embodiment of the invention suitable for running on the microelectrophoresis (2–10 micron) chip relies on the birefringent properties of DNA in a liquid crystal state.

Ultrathin layers of liquid crystals are routinely employed in the liquid crystal display industry. In certain orientations, liquid crystals have birefringent properties that cause substantial rotation of light and cause easily detectable light effects. Adapting this methodology to detection of DNA, it is observed that DNA in liquid crystal state acts as a birefringent material that will cause a substantially greater rotation of light than would the same amount of molecules in dilute solution based on optical activity. This embodiment therefore relies on the principle that tiny amounts of DNA can be detected if they are in liquid crystal state at the detection zone. A light polarization detector, positioned as illustrated in FIG. 5, can be used to detect extremely small amounts of unlabeled DNA if the DNA is brought into liquid crystal state at the detection site. Attaching magnetic beads to DNA and collecting the DNA under a strong magnetic field is one way to bring DNA into concentrations sufficient for the generation of a liquid crystal state.

A novel system for moving and separating different species of charged molecules such as nucleic acids has been disclosed which has advantages in the small scale manipulation of such species. It should be apparent that modifications to the several embodiments disclosed herein above will be made by those of ordinary skill when using the teachings of the present invention in different applications and situations, and the invention which is defined solely by the following claims should be in no way construed to exclude such modifications.

What is claimed is:

1. A microelectrophores is chip comprising a substrate having formed therein at least one separation channel for performing separation formed on a first major surface, said separation channel having a central region between two edges, a plurality of anodes and a plurality of cathodes disposed within each separation channel to induce an electric field within the channel, characterized in that the channel contains a homogeneous separation medium effective to act as obstacles to migration of biopolymers in a sample applied to the microelectrophoresis chip and in that the plurality of anodes and the plurality of cathodes include at least some anodes or cathodes disposed in the central region such that the anodes and cathodes can generate electric fields in at least two non-parallel directions within a plane parallel to the first major surface of the substrate.

2. The chip according to claim 1, wherein each individual pair of electrodes can be activated separately.

3. The chip according to claim 2, wherein the chip has a plurality of separation channels.

4. The chip according to claim 3, wherein each separation channel is from 1 to 10 $\mu$m in depth.

5. The chip according to claim 1, wherein the chip has a plurality of separation channels.

6. The chip according to claim 5, wherein each separation channel is from 1 to 10 $\mu$m in depth.

7. The chip according to claim 1, wherein each separation channel is from 1 to 10 $\mu$m in depth.

* * * * *